US009518940B2

(12) United States Patent
Nakano et al.

(10) Patent No.: US 9,518,940 B2
(45) Date of Patent: Dec. 13, 2016

(54) X-RAY DIFFRACTION METHOD AND PORTABLE X-RAY DIFFRACTION APPARATUS USING SAME

(75) Inventors: Asao Nakano, Kamakura (JP); Yoshinori Ueji, Akishima (JP)

(73) Assignee: RIGAKU CORPORATION, Tokyo (JP)

( * ) Notice: Subject to any disclaimer, the term of this patent is extended or adjusted under 35 U.S.C. 154(b) by 36 days.

(21) Appl. No.: 13/812,556

(22) PCT Filed: Jul. 28, 2011

(86) PCT No.: PCT/JP2011/067278
§ 371 (c)(1),
(2), (4) Date: Jan. 28, 2013

(87) PCT Pub. No.: WO2012/014982
PCT Pub. Date: Feb. 2, 2012

(65) Prior Publication Data
US 2013/0129051 A1 May 23, 2013

(30) Foreign Application Priority Data
Jul. 28, 2010 (JP) ................. 2010 169338

(51) Int. Cl.
*G01N 23/20* (2006.01)
*G01N 23/207* (2006.01)

(52) U.S. Cl.
CPC ............ *G01N 23/20* (2013.01); *G01N 23/207* (2013.01); *G01N 23/20008* (2013.01);
(Continued)

(58) Field of Classification Search
CPC ......... A61B 6/4405; A61B 6/46; A61B 6/461; G01N 23/20; G01N 23/20016; G01N 23/207; G21K 1/02; G21K 1/04; G21K 1/06; G21K 1/065
(Continued)

(56) References Cited

U.S. PATENT DOCUMENTS 5,497,008 A * 3/1996 Kumakhov ................. 250/505.1
7,646,847 B2 1/2010 He et al.
(Continued)

FOREIGN PATENT DOCUMENTS

CN 1864062 11/2006
JP 03-269251 11/1991
(Continued)

OTHER PUBLICATIONS

Bjeoumikhov et. al., A new microfocus x-ray source, iMOXS, for highly sensitive XRF analysis in scanning electron microscopes, Sep. 2005, X-Ray Spectrom., vol. 34, p. 493-495.*
(Continued)

*Primary Examiner* — Glen Kao
(74) *Attorney, Agent, or Firm* — Mattingly & Malur, PC

(57) ABSTRACT

A portable X-ray diffraction apparatus is provided which can be held by a person and on which an image of a spot to be measured can be viewed. The portable X-ray diffraction apparatus includes: X-ray irradiation means that irradiates a sample with collimated X-rays; diffracted X-ray detection means that detects a collimated portion of diffracted X-rays among X-rays diffracted from the sample by the irradiation of the X-rays with the X-ray irradiation means; and signal processing means that processes a signal outputted from the diffracted X-ray detection means. An X-ray diffraction method is used which includes: irradiating a sample with collimated continuous-wavelength X-rays; extracting a col-
(Continued)

limated portion of diffracted X-rays diffracted from the sample irradiated with the X-rays and condensing the extracted collimated portion of the diffracted X-rays; detecting, using an energy dispersive detection element, the condensed diffracted X-rays; and processing a signal detected by the detection element.

17 Claims, 6 Drawing Sheets

(52) U.S. Cl.
CPC . *G01N 2223/056* (2013.01); *G01N 2223/301* (2013.01); *G01N 2223/33* (2013.01)

(58) Field of Classification Search
USPC ..... 378/62, 70, 71, 78, 79, 81, 84, 98, 98.8, 378/102, 147, 160
See application file for complete search history.

(56) References Cited

U.S. PATENT DOCUMENTS

| | | |
|---|---|---|
| 2002/0191747 A1 | 12/2002 | Sato |
| 2004/0136496 A1* | 7/2004 | Mueller et al. ............... 378/72 |
| 2006/0088139 A1 | 4/2006 | Nakano et al. |
| 2006/0140343 A1 | 6/2006 | Gibson et al. |
| 2007/0058779 A1* | 3/2007 | Yokhin et al. ............... 378/71 |
| 2008/0159479 A1* | 7/2008 | Huang ................. G01N 23/20 378/73 |
| 2009/0213988 A1 | 8/2009 | Chen et al. |
| 2009/0274274 A1* | 11/2009 | He ...................... G01N 23/207 378/71 |
| 2011/0110493 A1* | 5/2011 | Radley ................. G01N 23/087 378/83 |

FOREIGN PATENT DOCUMENTS

| | | |
|---|---|---|
| JP | 2000-146872 | 5/2000 |
| JP | 2000-314709 | 11/2000 |
| JP | 2002-350373 | 12/2002 |
| JP | 2006-153767 | 6/2006 |
| JP | 2007-501395 | 1/2007 |
| JP | 2009-216631 | 9/2009 |
| JP | 2012-013423 | 1/2012 |

OTHER PUBLICATIONS

Feng et. al., VORTEX: A New High Performance Silicon Multi-cathode Detector for XRD and XRF Applications, Jan. 2004, Proc. SPIE, vol. 5198, p. 1, 2.*
Generation of X-rays [https://web.archive.org/web/20091108033409/http://pd.chem.ucl.ac.uk/pdnn/inst1/xrays.htm], Nov. 2009.*
Igor Zakharchenko et al., Methodology of Synchrotron Edxrd Strain Profiling, JCPDS—International Centre for Diffraction Data 2003, Advances in X-ray Analysis, vol. 46. pp. 98-105.
Jenkins & Synder, Introduction to X-ray Powder Diffractometry, 1966, John Wiley & Sons, Inc. pp. 178-203.
Office Action on corresponding Japanese Patent Application No. 2010-169338, mailed Mar. 11, 2014, with partial English language translation.
Office action in corresponding foreign Chinese Application No. 201180036808.X mailed Jun. 30, 2014.

* cited by examiner

X-RAY DIFFRACTION METHOD AND PORTABLE X-RAY DIFFRACTION APPARATUS USING SAME

TECHNICAL FIELD

The present invention is related to an X-ray diffraction method for analyzing a material by irradiating a sample with continuous wavelength X-rays generated by an X-ray tube and a portable X-ray diffraction apparatus using the same.

BACKGROUND ART

Applications have been established for X-ray diffraction methods as methods for identifying an unknown crystalline sample or for measuring a part of a large sample or a sample mounted on a substrate varying in kind. Under the circumstances, request has been growing larger for measuring devices which can be used outdoor to perform functions of analyzing devices which used to be used indoors. Thanks to the progress of electronic technology in recent years, power supply units and control circuits have been made smaller, lighter, and less power consuming. General X-ray diffraction methods, however, pose a problem that, when a sample is shifted out of position, their measurement accuracy or sensitivity is degraded. Hence, X-ray diffraction measurements have been performed using a mechanical angle measuring device called a goniometer to keep a sample correctly positioned.

As for the existing methods, the non-patent literature 1, for example, describes a measuring device which uses a goniometer to movably keep a sample, an X-ray source, and a detector in position. The patent literature 1, on the other hand, discloses a portable X-ray diffraction apparatus aimed at measuring X-ray diffraction at a specific part of a sample.

Also, in the non-patent literature 2, an X-ray diffraction measurement method is described in which an X-ray detector capable of X-ray photon energy analysis is used and in which no X-ray angle measuring device is used.

CITATION LIST

Patent Literature

Patent Literature 1: U.S. Pat. No. 7,646,847

Non Patent Literature

Non-patent literature 1: Jenkins & Snyder, Introduction to X-ray Powder Diffractometry, 1966, John Wiley & Sons, Inc. pp 178-203

Non-patent literature 2: International Center for Diffraction Data 2003, Advances in X-ray Analysis, Vol. 14 pp 98-105

SUMMARY OF INVENTION

Technical Problem

Generally, in X-ray diffraction measurement, X-ray diffraction intensities are measured at different X-ray diffraction angles using an X-ray detector, so that it has been necessary to perform measurement while changing the angles and positions of the sample and detector for every X-ray diffraction angle used. Therefore, the mechanical angle measuring device to be used is inevitably required to be heavy so as to keep an X-ray source and an X-ray detector securely in position and secure accuracy in changing their angles. It has, therefore, been difficult to use general X-ray diffraction apparatuses as portable apparatuses.

Energy analyzing type X-ray diffraction apparatuses which do not require angle changes use a large X-ray detector and, in such X-ray diffraction apparatuses, a sample and a detector are set apart so as to secure X-ray diffraction measurement accuracy. It has, therefore, been difficult to make energy analyzing type X-ray diffraction apparatuses with their weights and dimensions portable.

It has been difficult to make mechanical angle measuring devices like the one described in the non-patent literature 1 compact and light. As for the device described in the patent literature 1, it has been necessary to adopt a complicated configuration including a jig for attaching the device to a sample and plural two-dimensional detectors. Furthermore, according to the X-ray diffraction measurement method described in the non-patent literature 2 in which no X-ray angle measuring device is used, it is necessary to cool an X-ray detector to the temperature of liquid nitrogen, so that a large coolant container is required. In the method, it is also necessary to set a sample and the detector apart so as to secure measuring accuracy. Thus, the method is not necessarily applied to portable X-ray diffraction apparatuses.

The present invention has been made in view of the above problems with existing techniques, and it is an object of the present invention to realize a compact and light X-ray diffraction apparatus and provide an X-ray diffraction method and a portable X-ray diffraction apparatus using the method which enable data to be obtained with sufficiently stable accuracy even when the apparatus is used while being held by a person.

Solution to Problem

The present invention has been made, as described above, for realization of a compact and light portable X-ray diffraction apparatus which can be held by a person. Particularly, the invention has been made based on the following knowledge of the inventors. Namely, X-ray diffraction measurements used to be made under the conditions where the positional relationship among the incident X-rays, a sample, and the diffracted X-rays is securely maintained. For example, special X-rays (when a Cu target is used, wavelength of $K\alpha$ is 0.15418 nm) are radiated from an X-ray tube to a sample, and diffracted X-rays from the sample are measured. This measurement is performed, based on Bragg rule, using a mechanical angle setting device called a goniometer so as to accurately maintain a relationship among an X-ray tube, a sample and an X-ray detector. A mechanical goniometer is heavy, so that it is not an appropriate device to be used for measurement while being held by a person. Hence, an X-ray diffraction method and an X-ray diffraction apparatus using the method which, requiring no goniometer, enable measurement without being affected by shifting of the sample position if caused while the apparatus is held by a person have been demanded.

To achieve the above object, a portable X-ray diffraction apparatus according to the present invention includes: X-ray irradiation means that irradiates a sample with collimated X-rays; diffracted X-ray detection means that detects a collimated portion of diffracted X-rays among X-rays diffracted from the sample by the irradiation of the X-rays with the X-ray irradiation means; and signal processing means that processes a signal outputted from the diffracted X-ray detection means.

To achieve the above object, an X-ray diffraction method according to the present invention includes: irradiating a sample with collimated continuous-wavelength X-rays; selecting a collimated portion of diffracted X-rays diffracted from the sample irradiated with the collimated continuous-wavelength X-rays and condensing the selected collimated portion of the diffracted X-rays; detecting, using an energy dispersive detection element, the condensed diffracted X-rays; and processing a signal detected by the detection element.

Furthermore, to achieve the above object, an X-ray diffraction method according to the present invention includes: imaging a spot on a sample to be irradiated with X-rays; displaying an image thus imaged of the spot on the sample to be irradiated with X-rays; generating continuous wavelength X-rays using an X-ray tube; collimating the X-rays generated by the X-ray tube and obliquely irradiating the spot on a sample to be irradiated with the collimated X-rays, an image thereof is displayed; selecting and condensing a collimated portion of X-rays diffracted from the sample irradiated with the X-rays; detecting the selected and condensed diffracted X-rays using a detection element; and processing a signal detected by the detection element.

Advantageous Effects of Invention

The present invention, while making it possible to realize an X-ray diffraction apparatus of a size and weight to allow the apparatus to be carried and held by a person, can provide an X-ray diffraction method and a portable X-ray measuring apparatus using the method which enable X-ray diffraction measurement to be performed while observing a microscopic image of a specific part of a large sample on a display and which also enable stable X-ray measurement on such a specific part even when the sample surface is uneven or the sample position tends to move.

DESCRIPTION OF EMBODIMENTS

An embodiment of the present invention will be described in detail below with reference to the attached drawings.

Figure 1:
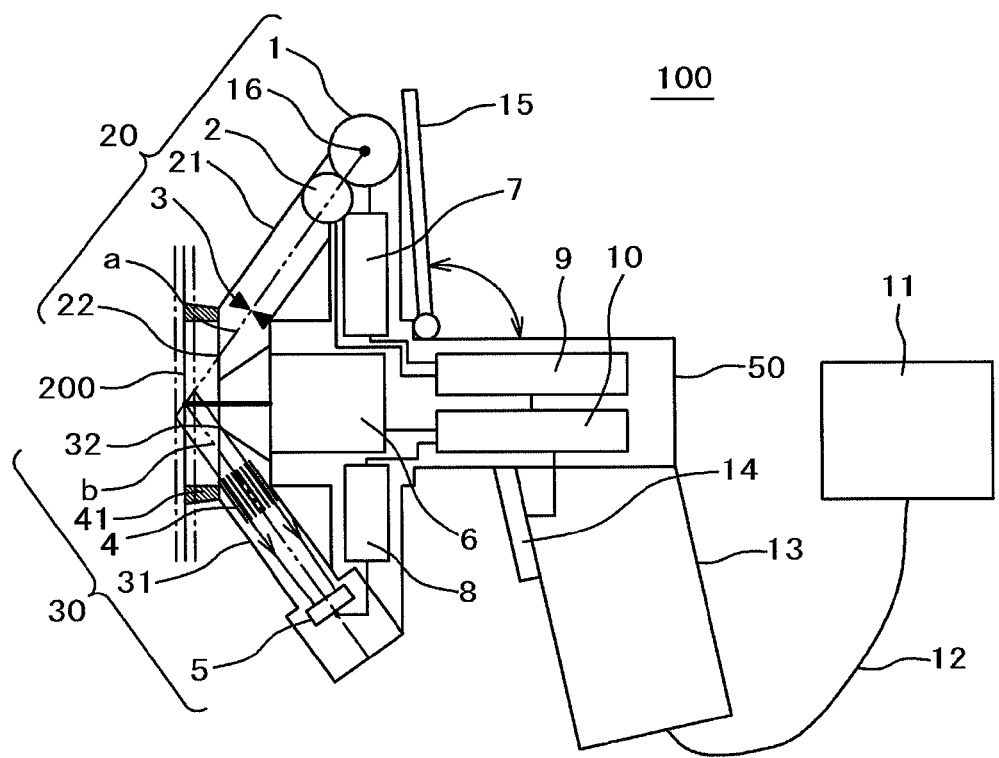
FIG. 1 is a diagram showing an overall configuration of a portable X-ray diffraction apparatus.

FIG. 1 is a diagram showing an overall configuration of a portable X-ray diffraction apparatus 100 according to an embodiment of the present invention. A housing cylinder 21 included in an X-ray irradiation section 20 is internally provided with an X-ray tube 1 for X-ray generation, an X-ray shutter 2, an X-ray optical element 3 for sample irradiation, and an X-ray transmission window 22. A housing cylinder 31 included in an X-ray detection section 30 is internally provided with an X-ray transmission window 32, a diffracted X-ray receiving optical element 4, and an X-ray detector 5. Furthermore, a sample observation section 6, a high-voltage power supply 7 for X-ray generation, a detector signal processing section 8, a high-voltage power supply and shutter opening/closing control section 9, a data processing and display control section 10, an electricity accumulation section 11, a power cable 12, a handle 13, a shutter opening/closing switch 14, and a collapsible data display section 15 are installed in a housing section 50.

The housing cylinder 21 included in the X-ray irradiation section 20 and the housing cylinder 31 included in the X-ray detection section 30 are mutually spatially connected and are both attached to the housing section 50. Also, the insides of the housing cylinder 21 included in the X-ray irradiation section 20 and the housing cylinder 31 included in the X-ray detection section 30 are evacuated by evacuation means, not shown. Furthermore, a ring-shaped X-ray shielding section 40 is attached to the surfaces, which is facing a sample 200, of the housing cylinder 21 included in the X-ray irradiation section 20 and housing cylinder 31 included in the X-ray detection section 30 so as to prevent the X-rays emitted from the X-ray irradiation section 20 to the sample 200 from looking outward. The contacting part 41 of the ring-shaped X-ray shielding section 40 comes in contact with the sample 200 to prevent the X-rays from leaking outward.

In the above configuration, on/off of the irradiation of the X-rays generated by the X-ray tube 1 to a sample is controlled by the shutter open/close switch 14 by operating the X-ray shutter 2 open/close. In a state where the shutter 2 controlled by the shutter open/close switch 14 is open, the X-rays generated by the X-ray tube 1 transmit through an X-ray optical element 3 and irradiate the sample 200.

The X-ray optical element 3 collimates the X-rays generated by the X-ray tube 1 to irradiate the sample 200 with the collimated X-rays. The X-ray optical element 3 used in the present embodiment is a slit with an opening size similar to the size of an X-ray focus 16 of the X-ray tube 1. The X-ray optical element 3 may be a parallel tube type monocapillary or it may be a polycapillary type element formed by bundling plural parallel tube type monocapillaries.

Part of the X-rays reflected (including scattered) from the sample irradiated with the X-rays enter a diffracted X-ray receiving optical element 4 and reach the X-ray detector 5. The diffracted X-ray receiving optical element 4 is a polycapillary type element formed by bundling plural parallel tube type monocapillaries. Among the X-rays entered into the diffracted X-ray receiving optical element 4, a collimated portion of the X-rays enters the polycapillary type diffracted X-ray receiving optical element 4. The X-rays entered into the polycapillary type diffracted X-ray receiving optical element 4 are transmitted through the polycapillary type diffracted X-ray receiving optical element 4 and enter the X-ray detector 5 capable of X-ray energy measurement where the X-rays diffracted from the sample are measured. The polycapillary type diffracted X-ray receiving optical element 4 is formed such that the X-rays outputted therefrom are condensed on the detection surface (not shown) of the X-ray detector 5.

An analog signal obtained by detecting X-rays at the X-ray detector 5 is digitized, for subsequent data processing, at the detector signal processing section 8 and is processed at the data processing and display control section 10. The results of the processing are displayed on the collapsible data display section 15. In the attached drawings, chain lines a and b each denotes an optical axis of an X-ray beam used for X-ray diffraction measurement in the portable X-ray diffraction apparatus 100 of the present embodiment.

Figure 2:
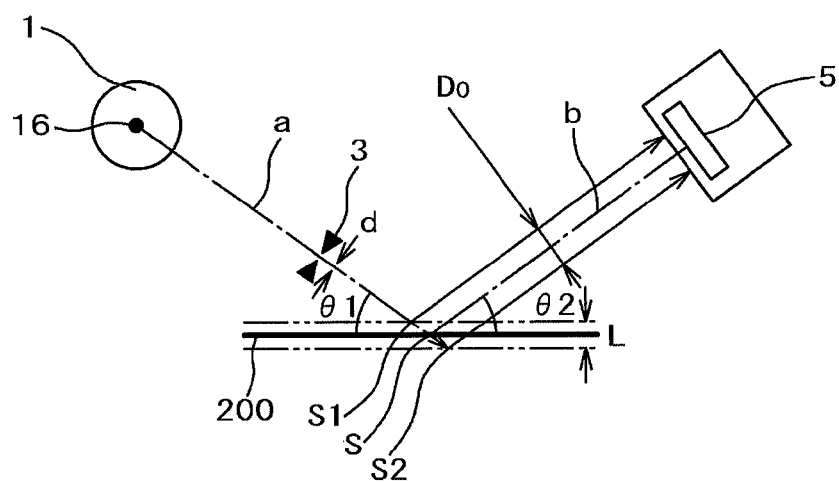
FIG. 2 is a diagram for explaining changes in diffracted X-ray position corresponding to changes in sample position in an X-ray diffraction apparatus.

In the present embodiment as shown in FIG. 1, an ideal position of the sample 200 relative to the optical axis a of an X-ray beam used for X-ray diffraction measurement is represented, in FIG. 2, by reference symbol S. In measurement performed using the portable X-ray diffraction apparatus 100 held by a person, keeping the sample 200 in an ideal position is difficult and the sample position is assumed to shift in a range denoted by L in FIG. 2. Namely, the position of the sample 200 to cause diffraction shifts between S1 and S2 (shifting width: L).

When it is assumed that nothing like the polycapillary type diffracted X-ray receiving optical element 4 shown in FIG. 1 is provided on the X-ray detection section 30 and that the X-rays reflected from the sample 200 travel straight in a direction defined by angle $\theta 2$, shifting width $D_0$ of the optical axis b of the diffracted X-ray beam as measured on a cross-sectional surface of the diffracted X-ray receiving optical element 4 is given by the following equation (1).

$$D_0 = L \times \sin(\theta 1 + \theta 2)/\sin((\theta 1 + \theta 2)/2) \qquad (1)$$

where $\theta 1$ is the incident angle of the X-rays to the sample from the X-ray optical element 3 and $\theta 2$ is the output angle of the X-rays diffracted from the sample. Both $\theta 1$ and $\theta 2$ are set to be in the range of 10 to 60 degrees.

When the sample position is shifted by L with the incident X-ray beam having diameter d, the surface of the X-ray detector 5 is required, to allow stable measurement of diffracted X-rays, to be larger than $D_1$ given by the following equation (2).

$$D_1 = d + D = d + L \times \sin(\theta 1 + \theta 2)/\sin((\theta 1 + \theta 2)/2) \qquad (2)$$

Next, the theory of the X-ray detection section 30 for collecting diffracted X-rays to be entered into the diffracted X-ray receiving optical element 4 shown in FIG. 1 will be partly described with reference to FIG. 3. The diffracted X-ray receiving optical element 4 used in the present embodiment is a polycapillary formed by bundling parallel tube type monocapillaries and has a parallel portion. A polycapillary changes the shape of an X-ray beam by making use of the total reflection of X-rays on the smooth inner surfaces of glass capillary tubes. The critical angle for X-ray total reflection at silica glass depends on the wavelength (energy) of the X-rays. When the X-ray wavelength is 0.083 nm and energy is 15 keV, the critical angle is about 0.125° (2.2 mrad).

Figure 3:
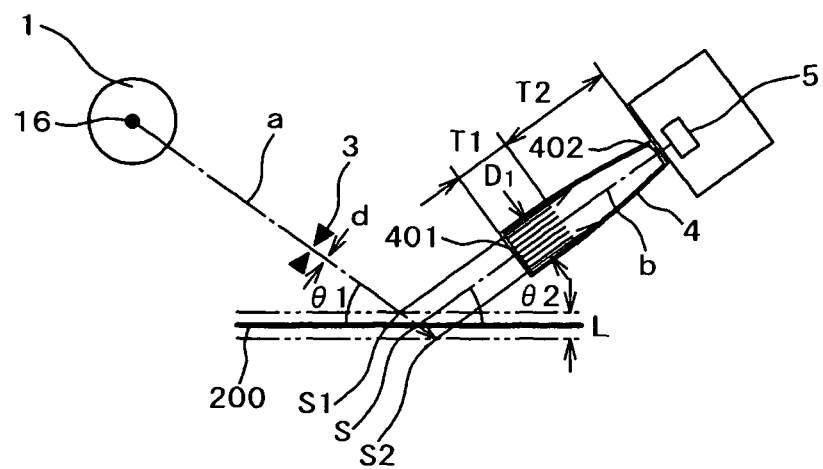
FIG. 3 is a diagram for explaining an angular width of a diffracted X-ray beam detected by a light receiving optical element and a reduction in diameter of an X-ray beam entering an X-ray detector in an X-ray diffraction apparatus.
Figure 4A:
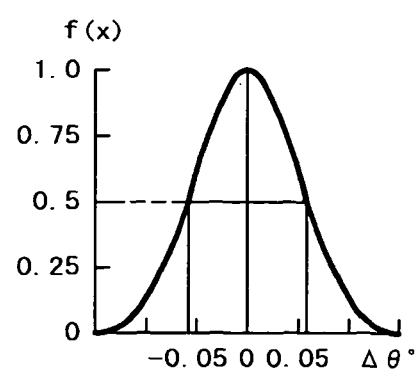
FIGS. 4A and 4B are diagrams for explaining an X-ray diffraction measuring module in the portable X-ray diffraction apparatus of the above embodiment.
Figure 4B:
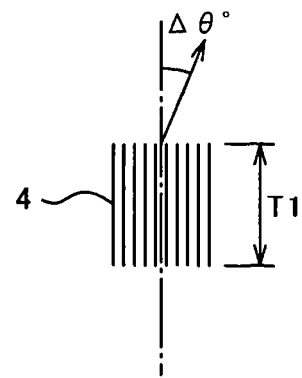

Referring to FIG. 3, when the polycapillary 4 is formed of bundled monocapillaries each with a glass tube inner diameter of 200 nm, an X-ray beam entering the polycapillary 4 at a total-reflection critical angle is totally reflected about once every 100 μm. Namely, it is totally reflected 100 times in the parallel polycapillary 4 with a length T1 of 10 mm. When, in this case, the reflectivity of total reflection is 0.99, most of the X-rays entering the polycapillary 4 from the incident end 401 thereof at an angle of 0.125° are absorbed inside the polycapillary. When an X-ray beam enters the polycapillary 4 at about 0.06°, i.e. about half the total-reflection critical angle, the number of times of total reflection in the parallel polycapillary 4 is halved to 50 resulting in an output intensity of about 50% for the X-ray beam outputted from the polycapillary. Thus, the relationship between the incident angle of X-ray beam and the intensity of X-ray beam output from the polycapillary is as shown in FIGS. 4A and 4B.

An X-ray beam with a wavelength shorter than 0.083 nm (with an energy higher than 15 keV) cannot pass through the parallel polycapillary unless it is entered with a still smaller incident angle. Because an X-ray beam with a long wavelength (with a low energy) is reflected at about the same reflectivity as an X-ray beam with a short wavelength, an X-ray beam with a long wavelength cannot pass through the parallel polycapillary, either, if it is entered into the polycapillary at a large incident angle to result in an increased number of times of total reflection. Hence, it is possible using the polycapillary 4 formed by bundling 10 mm long monocapillaries each with a glass tube inner diameter of 200 nm to select only a collimated X-ray beam with an angular divergence of about 0.12°.

The collimation operation performed, as described above, by the polycapillary 4 can also be performed using an ordinary multi-layered collimator. It is possible to use a compact multi-layered collimator.

An output end 402 of the polycapillary 4 is, as being described later, arranged such that the X-rays outputted from the output end 402 of the polycapillary 4 are condensed on the detection surface of the X-ray detector 5 so as to allow the detection surface to be smaller than $D_1$. The X-ray detector 5 can, therefore, be made smaller than in the configuration described with reference to FIG. 2.

Next, referring to FIG. 3, design of the parallel capillary type, diffracted X-ray receiving optical element 4 used in the present embodiment of the present invention will be described. The opening diameter $D_1$ on the incident end 401 of the X-ray receiving optical element 4 is given by the foregoing equation (2). When an X-ray beam has a diameter (d) of 1 mm, as a practical value, and the sample position shifting range (L) is also practically ±2 mm, the incident end 401 of the light receiving optical system is required to have an opening diameter ($D_1$) of about 9 mm. For use in place of the X-ray detector 5, silicon drift type semiconductor detectors (SSD) with a diameter of 10 mm have been commercially available as energy dispersive X-ray detectors. One of such SDDs may be directly attached, as the X-ray detector 5, to one end of the parallel polycapillary.

In the present embodiment, a light receiving optical element which, making use of a characteristic of a polycapillary, allows the X-ray detector 5 to have a reduced diameter is used. When the X-ray wavelength is 0.083 nm and energy is 15 keV as cited above, the total-reflection critical angle at a silica surface is 0.125° (2.2 mrad), so that the reflection angle can be set about 0.25° for one total reflection. By reducing the diameter of the polycapillary gradually and smoothly from the X-ray receiving part (X-ray incident side) thereof forming the polycapillary into a rotary ellipsoidal surface shape, the diameter of the diffracted X-ray beam can be reduced through total reflection at inner walls of the polycapillary. When the diffracted X-ray beam diameter is reduced by about 5° on a linear average basis through 20 times of total reflection, the opening diameter at the output end 402, spaced from the parallel polycapillary portion by T2=24 mm, of the polycapillary is about 6 mm. Thus, the diffracted X-ray beam entered through the incident end 401 with a diameter of 10 mm can be condensed and outputted from the output end 402. When, in this case, the reflectance of total reflection is assumed to be 0.99, the reduction in X-ray intensity is only about 20%.

Using a reduction optical element as described above makes it possible to use a detector with a diameter of 6 mm (with an area of 25 mm$^2$) (calculated values) instead of the X-ray detector 5 with a diameter of 10 mm (with an area of 80 mm$^2$). Currently, large silicon drift detectors are expensive while compact detectors are superior in terms of energy resolution characteristics, so that using a compact optical element is advantageous. Furthermore, when the polycapillary portion, formed to have a cross sectional shape like a rotary ellipsoidal surface, on the output end 402 is made 50 mm long (T2=50 mm), the opening diameter required on the output end 402 is about 2 mm, so that one of inexpensive mass-produced detectors with an area of 7 mm$^2$ (with a diameter of 3 mm) can be used.

The calculated values presented above are based on a total-reflection critical angle. The polycapillary used in the present embodiment of the present invention has a smooth rotary ellipsoidal surface shape and measures 50 mm in length and 10 mm in opening diameter at the incident end 401 which is reduced to measure 5 mm at the output end 402. What is required to this polycapillary is to condense the incident X-rays and output the condensed X-rays toward the X-ray detector 5. Namely, the polycapillary is not required to have a focusing function, so that it can be formed to have a smooth two-dimensionally curved surface.

Figure 5:
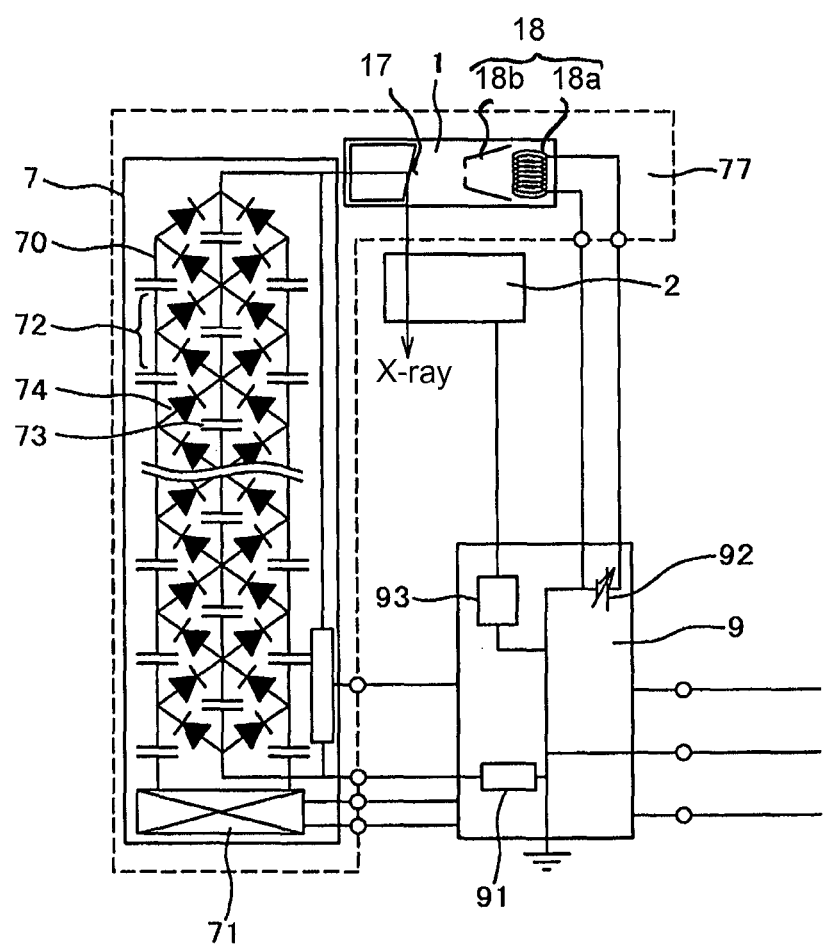
FIG. 5 is a diagram for explaining installation of a high-voltage power supply for an X-ray generation device (X-ray tube) in the portable X-ray diffraction apparatus of the above embodiment.

Next, with reference to FIG. 5, the X-ray tube 1 for X-ray generation, the high-voltage power supply 7 for X-ray generation and the high-voltage power supply and shutter open/close control section 9 used in the present embodiment of the present invention will be described. The X-ray tube 1 for X-ray generation is a compact X-ray tube using a ceramic insulator. It may also be a glass tube type X-ray tube. When, in cases where the overall circuit configuration is of an anode (a target) ground type, a hot cathode is used, a filament transformer of a high voltage insulation type is required. When the overall circuit configuration is of a cathode ground type, such a high voltage insulation type filament transformer is not required and having an advantage in reducing weight. Hence, in the present embodiment, the overall circuit configuration is of a cathode ground type. In FIG. 5, 17 is a cathode (target) and 18 is an anode including a filament 18a and electrode 18b. In the present embodiment, the heat (10 W) generated in the X-ray tube 1 is released by heat conduction via a high voltage insulator in the X-ray measurement apparatus.

The high voltage power supply 7 for X-ray generation includes a high-voltage boost rectifier circuit 70 which is a 12-stage Cockcroft-Walton circuit for full-wave rectification. For high-frequency power supply to the Cockcroft-Walton high-voltage boost rectifier circuit 70, a piezoelectric transformer 71 is used. A power of 4 kV-10 W is supplied by the single piezoelectric transformer 71 with an operating frequency of about 80 kHz. The piezoelectric transformer 71 is supplied with ±24 V at high frequency by the high-voltage power supply and shutter open/close control section 9. The high-voltage power supply and shutter open/close control section 9 is controlled by the data processing and display control section 10 so as to maintain a voltage set from outside. This control is performed using negative feedback based on an 80 kHz of high-frequency output circuit 91 and the voltage applied to the X-ray tube 1 for X-ray generation.

Figure 6A:
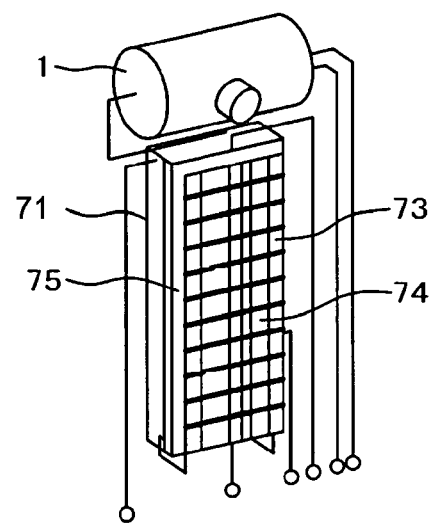
FIGS. 6A and 6B are diagrams for explaining installation of a high-voltage power supply for an X-ray generation device (X-ray tube) in a portable X-ray diffraction apparatus.
Figure 6B:
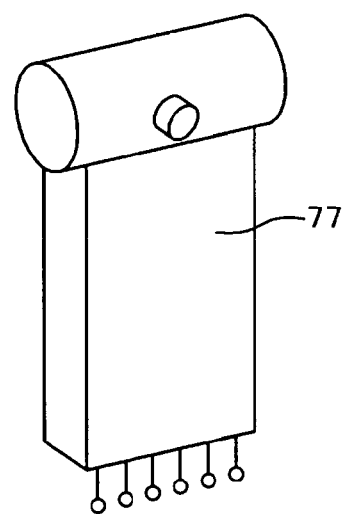

The high-voltage power supply and shutter open/close control section 9 includes a filament current control section 92 to control the current of the X-ray tube 1 and a switch circuit 93 for the X-ray shutter 2. The X-ray tube 1 and the high-voltage power supply 7 are integrally molded in a high-voltage power supply safety shield 77 as shown in FIG. 6B. To secure safety in manufacture and operation as well as in adjustment and inspection work, no voltage exceeding 24 V is applied to the external terminals of the high-voltage power supply safety shield 77.

In the present embodiment, the piezoelectric transformer 71 is adopted for its compactness and lightness, but a high-frequency coil transformer may also be used even though the transformer weight may somewhat increase.

Next, with reference to FIGS. 6A and 6B, the structure of the high-voltage power supply 7 for X-ray generation will be described. The high-voltage power supply 7 is formed, on a ceramic substrate 75 on which chip capacitors 73, chip diodes 74 and chip resisters (not shown in FIG. 6) are mounted. These chip components are ones designed for surface mounting so as to make the device compact. With the voltage of each stage of the Cockcroft-Walton high-voltage boost rectifier circuit 70 set to 4 kV, bridge circuits 72 each include a chip capacitor 73 with a withstanding voltage of 4 kV and two series-connected chip diodes 74 each with a withstanding voltage of 2 kV and make up a 12-stage full-wave rectifying circuit. Hence, in the present embodiment of the present invention, the rated working voltage and current are set to 40 kV and 0.25 mA, respectively, for a maximum applied voltage of 48 kV. A higher voltage can be made available by increasing the number of stages of the full-wave Cockcroft-Walton rectifying circuit.

The high-voltage power supply 7 for X-ray generation includes a chip resistor (not shown) for voltage division for voltage negative-feedback control and a piezoelectric transformer 71 mounted on the back side of the ceramic substrate 75. The piezoelectric transformer 71 being shaped like a thin rectangular shape is optimum for compact mounting. As compared with an electromagnetic high-frequency transformer, the piezoelectric transformer is, when considered for use in a compact device, superior in terms of electromagnetic noise. Because the piezoelectric transformer, by its principle, vibrates at high frequency (80 kHz), it is put in a case 77 of Teflon (registered trademark) for mounting on the substrate.

Figure 7A:
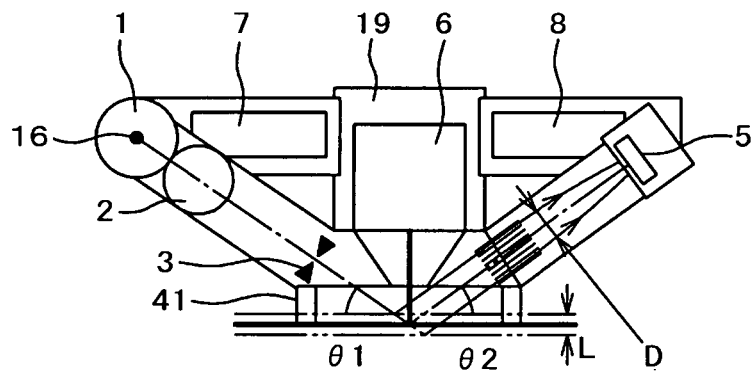
FIGS. 7A and 7B are diagrams for explaining how the weight of an X-ray generation device (X-ray tube) is reduced in the portable X-ray diffraction apparatus of the above embodiment.
Figure 7B:
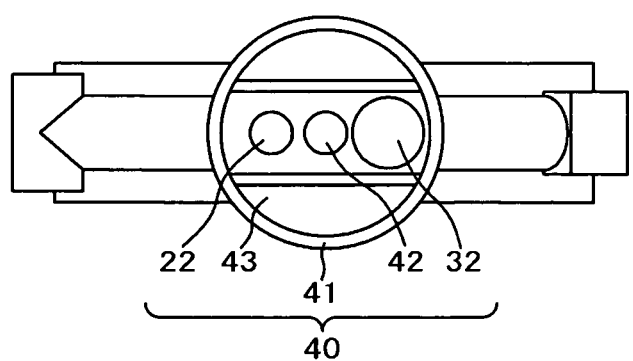

Next, with reference to FIGS. 7A and 7B, X-ray diffraction measurement performed according to the present embodiment will be described in detail. As shown in FIG. 7A, an X-ray beam generated at an X-ray focus 16 of the X-ray tube 1 for X-ray generation passes the X-ray optical element 3 for sample irradiation and is emitted to the sample 200 through the sample irradiating X-ray transmission window 22 provided on the sample side of the X-ray shielding section 40 shown in FIG. 7B. The contacting part 41 to be in contact with the sample 200 is made of heavy metal such as tungsten (W), tantalum (Ta) or lead (Pb) and is designed to prevent, when put in tight contact with the sample, the X-rays from leaking. Furthermore, to enhance safety during operation, plastic pieces (not shown) containing heavy metal are externally disposed to fit the shape of the sample as added means of X-ray leakage prevention. As a further safety arrangement, before X-ray emission is controlled by turning the shutter open/close switch 14 on/off, whether the contacting part 41 of the X-ray shielding section 40 is in contact with the sample is determined based on data obtained from a proximity switch (not shown) and the sample observation section 6 which performs optical measurement through a sample observation opening 42.

A part of the X-ray beam emitted to the sample 200 is diffracted by the sample 200 and enters, as a diffracted X-ray beam, the diffracted X-ray receiving optical element 4 via the diffracted X-ray detection and transmission window 32 and is led to the X-ray detector 5 for measuring X-ray diffraction data. In the case of the present embodiment, a molybdenum target is used in the X-ray tube 1 for X-ray generation and the sample irradiating X-ray angle (θ1) and the diffracted X-ray collection angle (θ2) are both set to 20°, making value d, which is crystal lattice spacing, measurable in the range of 0.7 nm to 0.07 nm. The X-ray wavelength range of 0.5 nm to 0.07 nm is used for the measurement. Since X-rays with a wavelength of 0.3 nm or longer, for example, X-rays with a wavelength of 0.5 nm (2.4 keV), are easily absorbed in the atmosphere, the insides of the housing cylinder 21 included in the X-ray irradiation section 20 and housing cylinder 31 included in the X-ray detection section 30 have been evacuated by unillustrated means. Even though, in the present embodiment, the housing cylinders have a completely vacuum-sealed structure, housing cylinders which are not kept vacuum-sealed and are exhausted using a pump only when using the apparatus may be used.

In the present embodiment, the housing cylinders 21 and 31 included in the X-ray irradiation section 20 and X-ray detection section 30, respectively, and the contacting part 41 of the X-ray shielding section 40 are mutually relatively rotatable and also the housing cylinders 21 and 31 included in the X-ray irradiation section 20 and X-ray detection section 30, respectively, and the housing section 50 are mutually relatively rotatable. This makes it possible to manually turn the housing section 50 and display, while the sample is being measured, measured data in the collapsible data display section 15. Continuing measurement while turning such sections makes it possible to collect averaged data, so that accurate and stable measurement is enabled. Furthermore, a direction in which a specific diffraction pattern appears can be determined, so that the orientation of crystals to cause X-ray diffraction from the sample can be determined.

Figure 8:
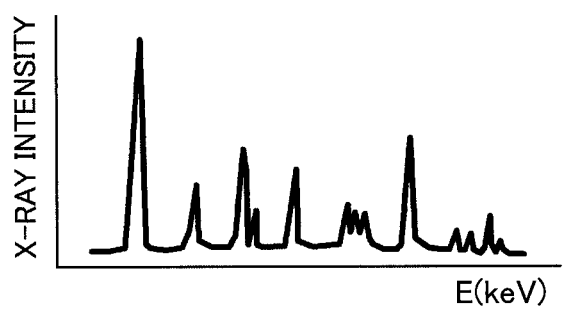
FIG. 8 is a graph showing an example of a detection signal detected by an X-ray detector.

An example of a detection signal outputted from the X-ray detector 5 having detected a diffracted X-ray beam is shown in FIG. 8. In the present embodiment, the X-ray detector 5 is an energy dispersive SDD. The SDD is a single pixel sensor. Therefore, making an X-ray beam diffracted from the sample 200 in a direction of diffraction angle θ2 enter the incident end 401 of the polycapillary 4 having a large diameter and detecting the diffracted X-ray beam after condensing it approximately to the pixel size of the X-ray detector 5 is effective in enhancing the detection sensitivity of the X-ray detector.

When a detection signal as shown in FIG. 8 is received, the detection signal processing section 8 calculates, by processing the signal, the crystal lattice spacing d of the sample 200.

The relationship between crystal lattice spacing d of the sample 200 and peak wavelength λ is, based on Bragg's condition, expressed as follows.

$$2d \sin \theta = \lambda \quad (3)$$

where θ is an X-ray incident angle.

The relationship between wavelength λ (nm) and energy E (keV) is expressed as follows.

$$\lambda = 1.24/E \quad (4)$$

When equation (4) is substituted into equation (3) with X-ray incident angle θ set to 30°, crystal lattice spacing d can be expressed as follows.

$$d = 1.24/E \quad (5)$$

Thus, crystal lattice spacing d can be determined based on a detection signal of photon energy as shown in FIG. 8 and equation (5).

Using the data obtained about crystal lattice spacing d and based on the relationship between internal stress and crystal lattice spacing d, the internal stress of the sample 200 can be determined.

When an anode target of molybdenum (Mo) is used in the X-ray tube 1, X-rays with an energy in the range of 3 to 15 keV can be detected, so that, based on equation (5), crystal lattice spacing d of the sample 200 can be detected in the range of 0.41 to 0.083 nm.

When an anode target of silver (Ag) is used in the X-ray tube 1, X-rays with an energy in the range of 3 to 20 keV can be detected, so that, based on equation (5), crystal lattice spacing d of the sample 200 can be detected in the range of 0.41 to 0.062 nm.

According to the present embodiment, it is possible to extract, using a polycapillary type optical element, only a collimated portion of the diffracted X-rays entered, after being diffracted from a sample irradiated with X-rays, in the housing cylinder 31 included in the X-ray detection section 30, so that, even when the sample surface is varied in height, a collimated portion of the diffracted X-rays can be securely detected. This makes it easy to attach a portable X-ray diffraction apparatus to a sample. Thus, a sample can be analyzed efficiently using a portable X-ray diffraction apparatus.

Since variations in the height of a sample surface are tolerated to a certain extent, even a rough-surfaced sample or a sample with a flexible wavy surface can be analyzed.

Also, since a polycapillary type optical element is used to condense diffracted X-rays to be detected, the X-ray detector to be used can be made compact. This allows the portable X-ray diffraction apparatus to be made more smaller and lighter.

INDUSTRIAL APPLICABILITY

The present invention is applicable to a portable X-ray diffraction apparatus for analyzing a sample by an X-ray diffraction method in which continuous wavelength X-rays generated by an X-ray tube are emitted to the sample.

REFERENCE SIGNS LIST

1 . . . X-ray tube for X-ray generation, 2 . . . X-ray shutter, 3 . . . X-ray optical element for sample irradiation, 4 . . . Diffracted x-ray receiving optical element, 5 . . . X-ray detector, 6 . . . Sample observation section, 7 . . . High-voltage power supply for X-ray generation, 8 . . . Detector signal processing section, 9 . . . High-voltage power supply and shutter opening/closing control section, 10 . . . Data processing and display control section, 11 . . . Electricity accumulation section, 12 . . . Power supply cable, 13 . . . Handle, 14 . . . Shutter open/close switch, 15 . . . Collapsible data display section, 20 . . . X-ray irradiation section, 21 . . . Housing cylinder, 22 . . . Sample irradiating X-ray transmission window, 30 . . . X-ray detection section, 31 . . . Housing cylinder, 32 . . . Diffracted X-ray detection and transmission window, 41 . . . X-ray shielding, sample contacting part, 42 . . . Sample observation opening, 50 . . . Housing section, 77 . . . High-voltage power supply safety shield

The invention claimed is:
1. A portable X-ray diffraction apparatus comprising:
X-ray irradiation means, including an X-ray tube, that irradiates a sample with continuous wavelength X-rays;
diffracted X-ray detection means that detects a collimated portion of diffracted X-rays, among X-rays diffracted from the sample by the irradiation of the X-rays with the X-ray irradiation means by condensing the collimated portion of the diffracted X-rays to have a smaller cross section than an opening of the diffracted X-ray detection means; and signal processing means that processes a signal outputted from the diffracted X-ray detection means, wherein:

an incident angle of the X-rays that irradiate the sample by the X-ray irradiation means and an emission angle of the diffracted X-rays detected by the diffracted X-ray detection means are able to be fixed in a range of values, the signal processing means detects a crystal lattice spacing of the sample by processing an output signal output from the diffracted X-ray detection means, detection of the crystal lattice spacing is unaffected by a positional shift between the sample and an optical center, wherein the optical center is a crossing point of a center axis of the X-rays that irradiate the sample and a center axis of the opening of the diffracted X-ray detection means, the portable X-ray diffraction apparatus is configured without using a goniometer and is able to be held by a human, the X-ray irradiation means includes:

the X-ray tube, which generates continuous wavelength X-rays, a shutter that opens and closes an optical path for the continuous wavelength X-rays generated by the X-ray tube, an irradiation optical means that collimates the continuous wavelength X-rays generated by the X-ray tube and obliquely irradiates the sample with the collimated X-rays, and an X-ray irradiation section housing cylinder internally provided with the X-ray tube, the shutter, and the irradiation optical means, the diffracted X-ray detection means includes:

a light receiving optical element that receives diffracted X-rays diffracted from the sample irradiated by the continuous wavelength X-rays generated by the X-ray tube and condenses the collimated portion of the diffracted X-rays, an X-ray detection element that detects the collimated diffracted X-rays condensed by the light receiving optical element, and an X-ray detection section housing internally provided with the light receiving optical element and the X-ray detection element, the portable X-ray diffraction apparatus further comprises a main body housing that holds an X-ray shielding section including a sample contact part and a display, and the X-ray irradiation section housing cylinder, the X-ray detection section housing, and the X-ray shielding section are mutually relatively rotatable, and the X-ray irradiation section housing cylinder, the X-ray detection section housing, and the main body housing are mutually relatively rotatable.

2. The portable X-ray diffraction apparatus according to claim 1, further comprising:

optical observation means for optically observing a spot on the sample to be irradiated with the X-rays; and display means that displays an optical image of the spot observed by the optical observation means, wherein the portable X-ray diffraction apparatus is configured to enable an X-ray diffraction measurement while presenting the optical image of the spot displayed on the display means.

3. The portable X-ray diffraction apparatus according to claim 1, wherein the irradiation optical means is formed of a slit or a polycapillary.

4. The portable X-ray diffraction apparatus according to claim 3, wherein, in the diffracted X-ray detection means, the light receiving optical element is formed of a polycapillary, wherein an input portion of the polycapillary that receives the diffracted X-rays diffracted from the sample is formed in parallel and an output portion of the polycapillary that outputs the diffracted X-rays is formed smaller in diameter than that of the input portion.

5. The portable X-ray diffraction apparatus according to claim 1, wherein an allowable range of the positional shift between the sample and the optical center is such that at least a part of the collimated portion of the diffracted X-rays, among the X-rays diffracted from the sample by the irradiation of the X-rays with the X-ray irradiation means, is detected by the X-ray detection element of the diffracted X-ray detection means.

6. The portable X-ray diffraction apparatus according to claim 5, wherein the X-ray detection element includes an energy dispersive detector.

7. The portable X-ray diffraction apparatus according to claim 6, wherein the energy dispersive detector is a silicon drift type semiconductor detector (SDD).

8. An X-ray diffraction method performed using a portable X-ray diffraction apparatus that includes a main body housing that holds an X-ray shielding section including a sample contact part and a display, an X-ray irradiation section housing cylinder, and an X-ray detection section housing, wherein the X-ray detection section housing and the X-ray shielding section are mutually relatively rotatable, and the X-ray irradiation section housing cylinder, the X-ray detection section housing, and the main body housing are mutually relatively rotatable, the method comprising:

obliquely irradiating, by an X-ray irradiation means, a sample with collimated continuous-wavelength X-rays, wherein the X-ray irradiation means includes the X-ray irradiation section housing cylinder which is internally provided with an X-ray tube that generates continuous-wavelength X-rays, a shutter, and an irradiation optical means that collimates the continuous wavelength X-rays generated by the X-ray tube and obliquely irradiates the sample with the collimated continuous-wavelength X-rays;

using the shutter to open and close an optical path for the continuous-wavelength X-rays generated by the X-ray tube;

receiving, by a light receiving optical element, a collimated portion of diffracted X-rays diffracted from the sample irradiated with the collimated continuous-wavelength X-rays, wherein the light receiving optical element is included in a diffracted X-ray detection means that includes the X-ray detection section housing internally provided with the light receiving optical element and an energy dispersive X-ray detection element;

condensing, by the light receiving optical element, the received collimated portion of the diffracted X-rays;

detecting, using the energy dispersive X-ray detection element, the condensed diffracted X-rays;

processing a signal detected by the energy dispersive detection element; and detecting a crystal lattice spacing of the sample by processing an output signal output from the diffracted X-ray detection means, which detects at least a part of the collimated portion of the diffracted X-rays, wherein shifting of a position on the sample of an optical center does not affect the detecting, wherein the optical center is a crossing point of a center axis of the X-rays that irradiate the sample by the X-ray irradiation means and a center axis of the opening of the diffracted X-ray detection means.

9. The X-ray diffraction method according to claim 8, wherein:
the collimated continuous-wavelength X-rays are formed using a slit or a first polycapillary included in the irradiation optical means; and
the condensing the selected collimated portion of the diffracted X-rays is performed by inputting the diffracted X-rays diffracted from the sample to an input portion of a second polycapillary included in the light receiving optical element and outputting a parallel portion of the X-rays input to the second polycapillary from an output portion of the second polycapillary that is smaller in diameter than the input portion.

10. The X-ray diffraction method according to claim 8, wherein an allowable range of the shifting of the position between the sample and the optical center is such that at least a part of the collimated portion of the diffracted X-rays, among the X-rays diffracted from the sample, is detected by the energy dispersive X-ray detection element of the diffracted X-ray detection means.

11. The X-ray diffraction method according to claim 8, further comprising detecting the condensed diffracted X-rays while the main body housing is rotated.

12. An X-ray diffraction method performed using a portable X-ray diffraction apparatus that includes a main body housing that holds an X-ray shielding section including a sample contact part and a display, an X-ray irradiation section housing cylinder, and an X-ray detection section housing, wherein the X-ray detection section housing and the X-ray shielding section are mutually relatively rotatable, and the X-ray irradiation section housing cylinder, the X-ray detection section housing, and the main body housing are mutually relatively rotatable, the method comprising:
optically measuring a spot on a sample to be irradiated with X-rays;
displaying an image of the spot on the sample to be irradiated with X-rays;
generating continuous wavelength X-rays using an X-ray tube that generates continuous wavelength X-rays, wherein the X-ray tube is included in X-ray irradiation means which includes the X-ray irradiation section housing cylinder which is internally provided with the X-ray tube, a shutter, and an irradiation optical means that collimates the continuous wavelength X-rays generated by the X-ray tube and obliquely irradiates the sample with the collimated continuous-wavelength X-rays;
using the shutter to open and close an optical path for the continuous-wavelength X-rays generated by the X-ray tube;
collimating, by the irradiation optical means, the continuous wavelength X-rays generated by the X-ray tube;
obliquely irradiating, by the irradiation optical means, the spot on the sample with the collimated continuous wavelength X-rays;
displaying an image of the spot on the display;
selecting a collimated portion of diffracted X-rays diffracted from the sample irradiated with the collimated continuous wavelength X-rays by inputting the diffracted X-rays into an incident end of a polycapillary formed at a parallel shaped portion of the polycapillary, wherein the polycapillary is included in a diffracted X-ray detection means that includes the X-ray detection section housing internally provided with the polycapillary and an energy dispersive X-ray detection element;
condensing the selected collimated portion of the diffracted X-rays by outputting the diffracted X-rays from an output end of the polycapillary, which is smaller in cross section than the incident end of the polycapillary;
detecting, using the energy dispersive detection element, the condensed collimated portion of the diffracted X-rays irrespective of a variation in height of a surface of the sample; and
processing a signal detected by the energy dispersive detection element that detects the condensed collimated portion of the diffracted X-rays to determine a crystal lattice spacing irrespective of the variation in height of the surface of the sample.

13. The X-ray diffraction method according to claim 12, wherein the X-rays generated by the X-ray tube are collimated using a slit or another polycapillary as the irradiation optical means.

14. The X-ray diffraction method according to claim 12, wherein the incident end of the polycapillary of the diffracted X-ray detection means has a diameter larger than a diameter of the energy dispersive X-ray detection element.

15. The X-ray diffraction method according to claim 12, wherein the condensed collimated portion of the diffracted X-rays are detected by the energy dispersive detection element, which is a single pixel sensor.

16. The X-ray diffraction method according to claim 12, wherein an allowable range of the variation in height of the surface of the sample is such that at least a part of the collimated portion of the diffracted X-rays, among the X-rays diffracted from the sample, is detected by the energy dispersive detection element.

17. The X-ray diffraction method according to claim 12, further comprising detecting the condensed collimated portion of the diffracted X-rays while the main body housing is rotated.

* * * * *